United States Patent [19]

Alfery

[11] Patent Number: 5,040,532
[45] Date of Patent: Aug. 20, 1991

[54] CONTINUOUS POSITIVE AIRWAY PRESSURE DEVICE FOR THORACIC SURGERY UTILIZING ONE-LUNG ANESTHESIA

[76] Inventor: David D. Alfery, 5543 S. Stanford Dr., Nashville, Tenn. 37215

[21] Appl. No.: 318,409
[22] Filed: Mar. 3, 1989
[51] Int. Cl.⁵ ............................................. A61M 16/00
[52] U.S. Cl. ........................ 128/207.15; 128/207.16; 128/205.11
[58] Field of Search ............... 128/203.12, 203.22, 128/204.18, 205.24, 207.14, 207.15, 207.16

[56] References Cited

U.S. PATENT DOCUMENTS

| | | | |
|---|---|---|---|
| 2,378,468 | 6/1945 | Deming | 128/205.11 |
| 3,017,881 | 1/1962 | Smith | 128/205.13 |
| 3,786,809 | 1/1974 | Kitrilakis | 128/205.26 |
| 3,850,171 | 11/1974 | Ball et al. | 128/205.11 |
| 3,906,996 | 9/1975 | DePass et al. | 137/893 |
| 3,913,607 | 10/1975 | Price | 128/205.11 |
| 3,977,432 | 8/1976 | Vidal | 128/205.11 |
| 4,036,253 | 7/1977 | Fegan et al. | 128/205.11 |
| 4,098,290 | 7/1978 | Glenn | 137/604 |
| 4,244,363 | 1/1981 | Moore, Jr. et al. | 128/205.17 |
| 4,249,527 | 2/1981 | Ko et al. | 128/204.18 |
| 4,261,355 | 4/1981 | Glazener | 128/204.25 |
| 4,266,540 | 5/1981 | Panzik et al. | 128/205.11 |
| 4,502,481 | 3/1985 | Christian | 128/205.24 |
| 4,593,688 | 6/1986 | Payton | 128/200.28 |
| 4,598,706 | 7/1986 | Darowski et al. | 128/205.24 |
| 4,643,183 | 2/1987 | Seilinger | 128/204.17 |
| 4,848,333 | 7/1989 | Waite | 128/205.11 |

OTHER PUBLICATIONS

Benum of, Jonathan, Anesthesia for Thoracic Surgery, 1987, W. B. Saunders Co., pp. 278, 283.
Brown, et al., "Improved Ventilation During Thoracotomy With Selective PEEP To The Dependent Lung," Anesthesia and Analgesia, vol. 56, No. 1, 1977, pp. 26-30.

Primary Examiner—Aaron J. Lewis
Attorney, Agent, or Firm—Sughrue, Mion, Zinn, Macpeak & Seas

[57] ABSTRACT

A device for the application of continuous positive airway pressure (CPAP) delivering 100% oxygen during thoracic surgery utilizing one-lung anesthesia. The device comprises a hollow, cylindrical member serving as a conduit for oxygen. One end of the device is connected to a source of oxygen delivered at a constant flow rate. The opposite end attaches to one lumen of a double-lumen endotracheal tube. A removable cap is attached to the device. If the cap is removed, a breathing bag can be attached for allowing the periodic expansion of the lung connected to the apparatus. A venting device is provided to allow the egress of oxygen under pressure. By changing a venting orifice, varying degrees of pressure of oxygen will be delivered to the one lumen of the double-lumen tube.

15 Claims, 3 Drawing Sheets

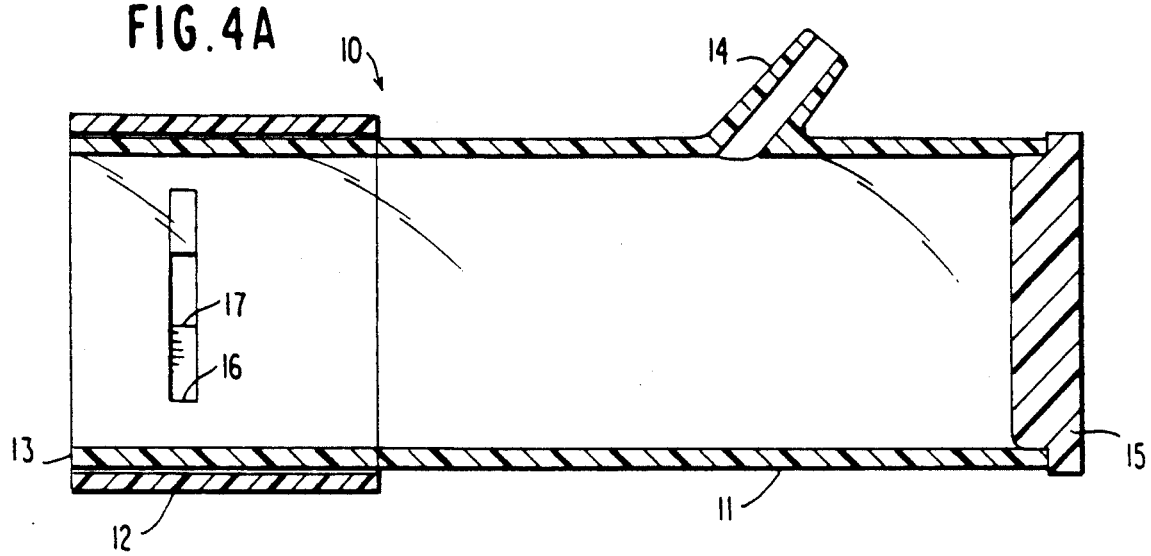
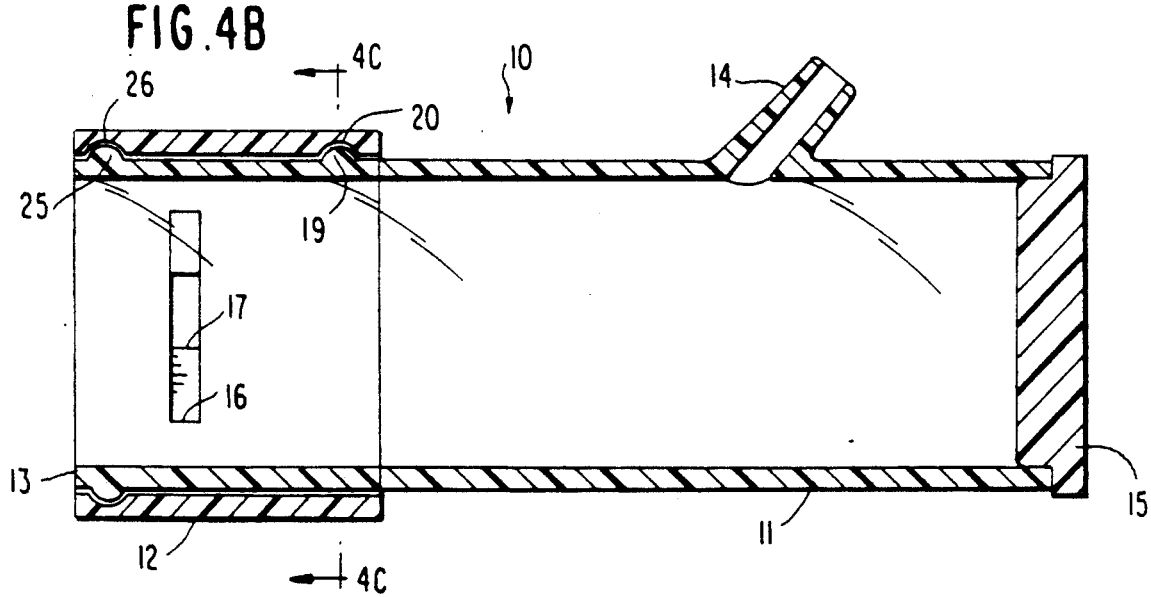
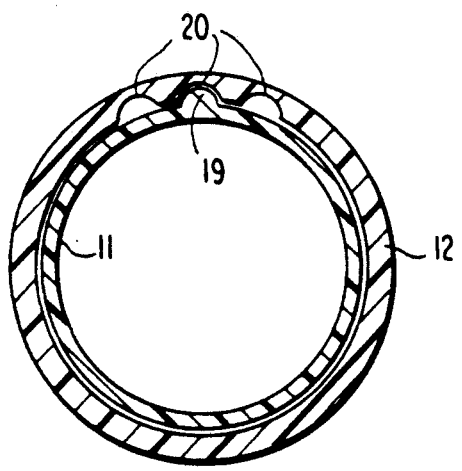

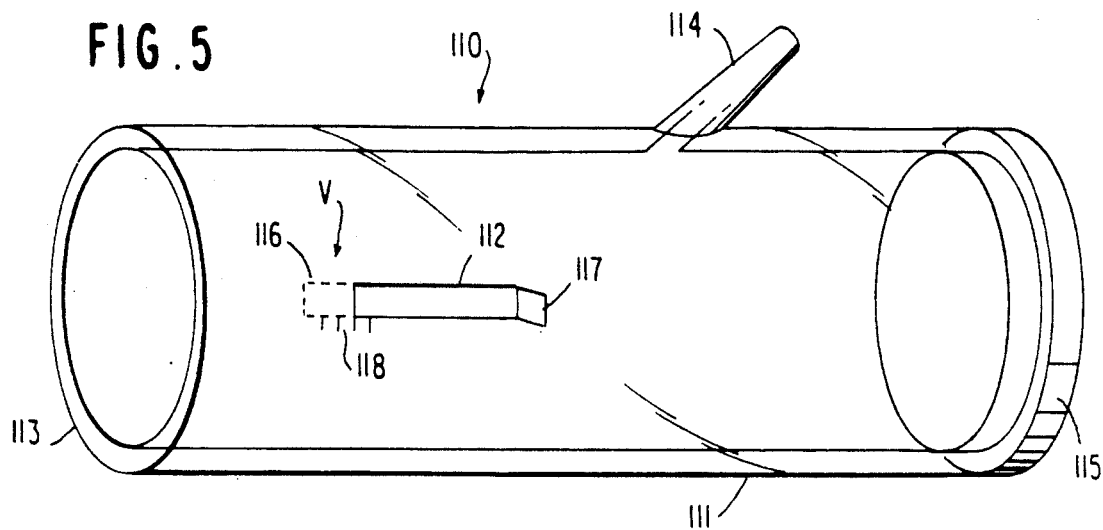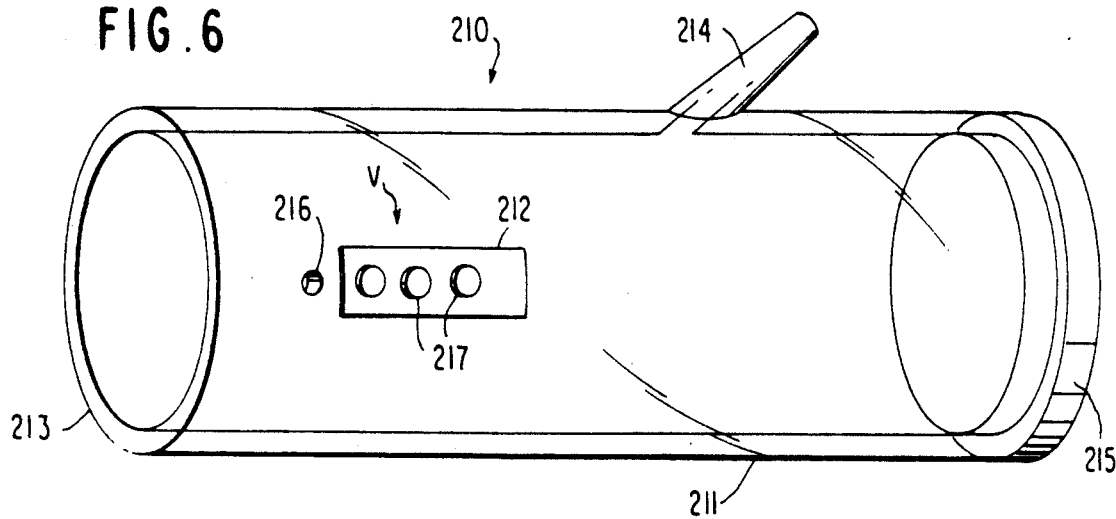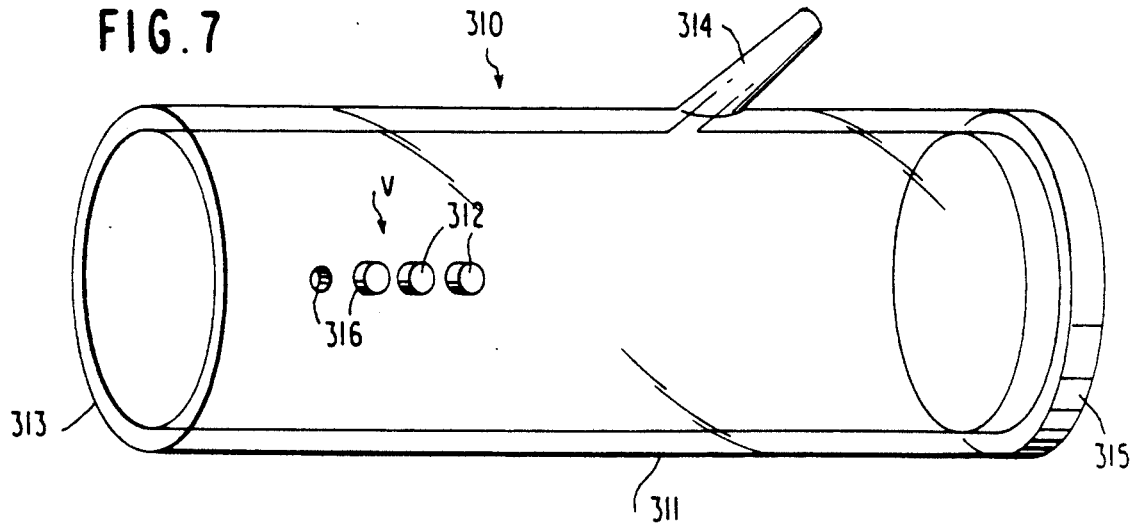

CONTINUOUS POSITIVE AIRWAY PRESSURE DEVICE FOR THORACIC SURGERY UTILIZING ONE-LUNG ANESTHESIA

BACKGROUND OF THE INVENTION

My invention provides a unique, inexpensive, hygienic, simple, precise and safe way to provide 100% oxygen by continuous positive airway pressure (CPAP) to the non-ventilated, non-dependent lung during thoracic operations utilizing one-lung ventilation. Approximately seventy-five thousand thoracic operations are done annually in the United States utilizing one-lung anesthesia. Many thousands more are done utilizing conventional two-lung anesthesia and two-lung ventilation because practitioners wish to avoid the potential for life-threatening hypoxemia (under-oxygenation of the blood) which is associated with one-lung anesthesia.

"One-lung anesthesia" is a term which is used to describe patients who undergo thoracic surgery in which only the dependent, non-operated lung is ventilated, no matter how the anesthesia is given. In general, the anesthetic is given intravenously or by inhalation or, most commonly, by a combination of these two techniques. In fact, then, "one-lung anesthesia" might be better termed "one-lung ventilation in conjunction with anesthesia for thoracic operations".

Since only one lung is ventilated, a special technique must be used to physically separate the lungs. Most commonly, this separation is accomplished by using a double-lumen endotracheal tube. As shown in FIG. 1, this tube 1 has two separate lumens or breathing channels 2 and 3 delivering oxygen and anesthetic gas through an anesthesia circuit 4 to each of the lungs 5, a Y-connector 6 to connect the proximal ends of the channels together, and a clamp 7 for disconnecting one channel from the Y-connector. When gases and oxygen are delivered to the Y-connector, both lungs are normally ventilated with fresh gas flowing through the separate channels 2 and 3 to the respective lungs. However, if the upper leg of the Y-connector 6 is clamped, then only the lower lung 8 is ventilated. Further, when the side which is clamped is opened to room air by opening a cap (not shown) on the channel 2, the lung associated with that channel will collapse. The foregoing procedure is what is done during thoracic surgery. By doing so, one creates a compact, collapsed upper lung 9 for the surgeon to operate on. More important, the operated lung 9 is no longer expanding and collapsing since no ventilation is being delivered to that side (anesthetized patients undergoing thoracic operations are paralyzed with neuromuscular blocking drugs and cannot breathe for themselves).

Thus, during one-lung anesthesia, the lungs are separated by the anesthesiologist providing positive pressure ventilation to the dependent lower lung 8 while the surgeon operates on the small, still, non-ventilated, non-dependent upper lung 9. By definition, ventilation is the physiologic process whereby lung inhalation (or inflation) and exhalation (or deflation) occur; during lung surgery, ventilation is caused by the intermittent delivery of gas under pressure by the anesthesiologist. Ventilation serves two purposes. First, oxygen is delivered to the lung where it is taken up by the blood and carried out to the body for use in metabolic processes. Second, carbon dioxide, an end-product of the body's physiologic metabolic processes, is excreted.

When one-lung ventilation is initiated during thoracic operations, the dependent ventilated lower lung 8 still participates in the delivery of oxygen to the blood. However, the non-ventilated, non-dependent upper lung 9 no longer participates in gas exchange. Ideally, all the de-oxygenated blood returning to the right side of the heart and going to the lungs encounters alveoli or air sacs which are filled with oxygen (because they have been ventilated), thereby allowing the de-oxygenated blood to replenish its supply. In the situation of one-lung ventilation, however, the blood which passes through the non-ventilated lung remains de-oxygenated and mixes with the blood passing through the ventilated lung. Thus, there is invariably a fall in overall oxygenation of the blood as compared to situations of two-lung ventilation. The body has a number of physiologic mechanisms which tend to divert blood to the ventilated lung and away from the non-ventilated lung and thereby reduce the amount of poorly oxygenated blood which mixes with that which is well oxygenated. In addition, anesthesiologists employ a number of maneuvers to maximally oxygenate the blood which flows to the single-ventilated lung (such as using 100% oxygen); however, there is a significant percentage of patients in which undertaking one-lung ventilation will cause life-threatening hypoxemia to occur.

When hypoxemia occurs during one-lung ventilation, the obvious solution is to reinstitute ventilation to the non-dependent (upper) lung. However, this situation may cause hazardous interference with the surgical procedure. Fortunately, one can still provide oxygen under gentle pressure (low levels of CPAP) to the non-dependent lung without actually ventilating (that is, without actually inflating and deflating) that lung. Gently stenting open alveoli with oxygen under constant, non-varying pressure allows the blood flowing through this non-ventilated lung now to become well oxygenated, thereby alleviating the hypoxemia. Because the pressure is constant and unvarying, the lung is not moving (and thus not ventilating), and the surgeon is able to carry out the operation with a minimum of interference. In the situation of ventilation of the dependent lung along with such CPAP oxygenation (without ventilation) of the non-dependent lung, oxygenation of the blood is occurring via both lungs while active carbon dioxide removal is occurring via only the ventilated lung. The reason for this is that active inhalation and exhalation are needed to provide carbon dioxide removal, while it is necessary only to present oxygen to the alveoli to allow oxygenation. Fortunately, patients can tolerate a modest buildup of carbon dioxide without serious harm.

Unfortunately, even though there exists a physiological solution to the problem of hypoxemia during one-lung ventilation (namely, non-dependent lung CPAP oxygenation), there is no commercially available, fully assembled, inexpensive device for implementing the solution. While several CPAP systems have been described in the anesthesia literature, the problem with all such systems is that they are "homemade" devices which must be assembled by the practitioner from individually obtained components. Most of the devices described, such as those taught by Benumof in his *Anesthesia for Thoracic Surgery*, published in 1987 by W. B. Saunders Company, include a pressure-measuring gauge along with a "pop-off" regulating valve and oxygen tubing; when fully assembled, most such devices cost well over $100. In addition, they are bulky and cumbersome to use.

There are several consequences of the above problem. First, very few practitioners have taken the time, trouble and expense required to procure and assemble for themselves a device which allows CPAP oxygenation to the non-dependent lung. When these individuals encounter hypoxemia during one-lung ventilation, either they "get by" with varying degrees of under-oxygenation of the patient or they resume two-lung ventilation and thereby interfere with the operation being performed. Alternatively, many practitioners elect never to use one-lung ventilation anesthesia techniques for fear of encountering hypoxemia and not having the means (a CPAP device) to treat it properly, thereby imposing a serious risk to certain patients since it is well established that physical lung separation with one-lung ventilation is mandated for certain operations (lung abscess or bronchopleural cutaneious fistula, for example). Thus, one subset of patients is being denied a required procedure for fear of a potential complication, while another subset is being given the procedure without the means to treat that complication should it occur.

Another continuous positive airway pressure administrating device has been proposed in U.S. Pat. No. 4,249,527 (Ko et al.) which relates to a complicated system for administering CPAP to patients, such as new born infants suffering from idiopathic respiratory-distress syndrome. This system, which includes a tube attached to a source of fresh air under pressure, a hose connecting the tube with a pressure control valve assembly 142, and a nasal cannula for delivering CPAP to the patient, may be controlled by adjusting the control valve 142 to expose more or fewer of openings 188, 190 to the atmosphere thereby venting more or less carbon dioxide exhaled by the patient. Thus, CPAP is being administered to both lungs while the patient is actively ventilating. Further, the valve 142 may be completely closed off or opened to provide an unlimited continuum of pressure settings. Therefore, such a system is not suitable for use with anesthetized patients undergoing one-lung anesthesia.

U.S. Pat. No. 4,261,355 (Glazener) discloses a constant positive pressure breathing apparatus for use with patients undergoing either spontaneous respiration or mechanical ventilation. If one regulates the mass flow rate of gas from a remote reservoir into a nozzle, variable levels of constant positive airway pressure can be maintained. Thus, this apparatus has a drawback in that the only way to vary the airway pressure is to control gas flow rate. Also, Glazener's device is used with a standard endotracheal tube as opposed to a double-lumen endotracheal tube.

U.S. Pat. Nos. 4,643,183, 4,593,688 and 4,098,290 disclose various breathing related apparatuses including valve means.

U.S. Pat. No. 4,598,706 discloses an apparatus for independent ventilation of two lungs by using a positive end-expiratory pressure (PEEP) valve. Also, an article, entitled "Improved Ventilation During Thoracotomy with Selective PEEP to the Dependent Lung" by Brown, et al., published in Anesthesia and Analgesia in 1977 (Vol. 56, No. 1), discloses a device for supplying PEEP to the dependent lung during two-lung ventilation in thoracotomy patients.

U.S. Pat. Nos. 3,017,881, 3,786,809, 3,906,996, 4,244,363, 4,266,540 and 4,502,481 are of background interest with respect to the present invention.

SUMMARY OF THE INVENTION

My invention provides an apparatus which remedies the problem of providing CPAP oxygenation to the non-ventilated lung. Briefly, oxygen flowing at a constant rate (5 L/minute) is connected to the nozzle of a hollow, cylindrical device. The opposite end connects to the lumen of a double-lumen endotracheal tube which in turn leads to a lung which is not being ventilated. A graduated vent opening allows the escape of oxygen under pressure. Pressure within the system ranges from 5 to 10 cm. $H_2O$ and the oxygen pressure will obviously be transmitted to the lung as well. This gentle and constant pressure will allow some alveoli to be stented open, thereby allowing the blood passing through them to become oxygenated. Typically, less than 1% of the oxygen will flow into the lung while more than 99% escapes through the vent. As the level of CPAP is increased, more and more alveoli become stented open to allow progressive improvements in oxygenation. In this way, situations of critical hypoxemia are remedied. Surgery is able to continue unimpeded because no active ventilation is occurring; that is, the operated lung remains relatively small and constant in size and configuration since no active expansion and contraction occur.

A small removable cap is present on the end of the apparatus. When the cap is removed, one can attach an anesthesia bag which will fill with oxygen to the pressure generated within the system. From time to time, it may be helpful to initially open previously closed alveoli by squeezing the bag and transiently generating greater pressure within the system. When the pressure then falls to that set by the apparatus, the now opened alveoli will be kept open by the CPAP generated by the device.

In one embodiment of my invention, the CPAP device includes a shorter outer cylinder which is snugly and rotatably disposed on one end of a long hollow inner cylinder. This end of the long inner cylinder is designed to fit onto the proximal end of one lumen of a double-lumen endotracheal tube. The removable cap is inserted in the opposite end of the long inner cylinder. A cylindrical fitting extends from a side portion of the long inner cylinder for attachment to an oxygen tube connected to a source of oxygen delivered at a constant flow rate.

Both the inner and outer cylinders have an elongated slot cut in them to form means for continuously venting the oxygen such that, when the cylinders are rotated with respect to each other, the slots cooperate to form a larger or smaller opening to provide for varying degrees of pressure of the oxygen delivered to the single lumen and, in turn, to the non-ventilated lung of a patient during thoracic surgery. The slots are always at least partially in line, so that there is always a means for permitting oxygen to escape the device.

In one modification of my invention, the venting means takes the form of a tab slidable in an elongated slot formed in a single hollow cylindrical member in such a manner that there always is some degree of opening of the slot.

In another modification, the venting means takes the form of a series of aligned holes provided in a single hollow cylindrical member. Further, a plastic strip having a series of corresponding projections thereon is arranged such that the projections sealingly engage a variable number of the holes but in such a manner that at least one hole always being open.

In still another modification, the venting means is similar to that described above, except several individual closure members are employed to close a variable number of holes with at least one hole always being open.

BRIEF DESCRIPTION OF THE DRAWINGS

Other features and advantages of the invention will be apparent from the following description taken in connection with the accompanying drawings, wherein:

FIG. 4A is a sectional view taken along the plane 4A—4A of FIG. 3 and looking toward the opening formed by the aligned slots;

FIG. 4B is a sectional view, similar to FIG. 4A, but showing an alternative embodiment;

FIG. 4C is a sectional view taken along the plane 4C—4C of FIG. 4B;

FIG. 5 is a perspective view of another embodiment of the CPAP device of the invention;

FIG. 6 is a perspective view of a further embodiment of the CPAP device of the invention; and FIG. 7 is a perspective view of a still further embodiment of the CPAP device of the invention.

DETAILED DESCRIPTION OF THE PREFERRED EMBODIMENTS

Figure 2:
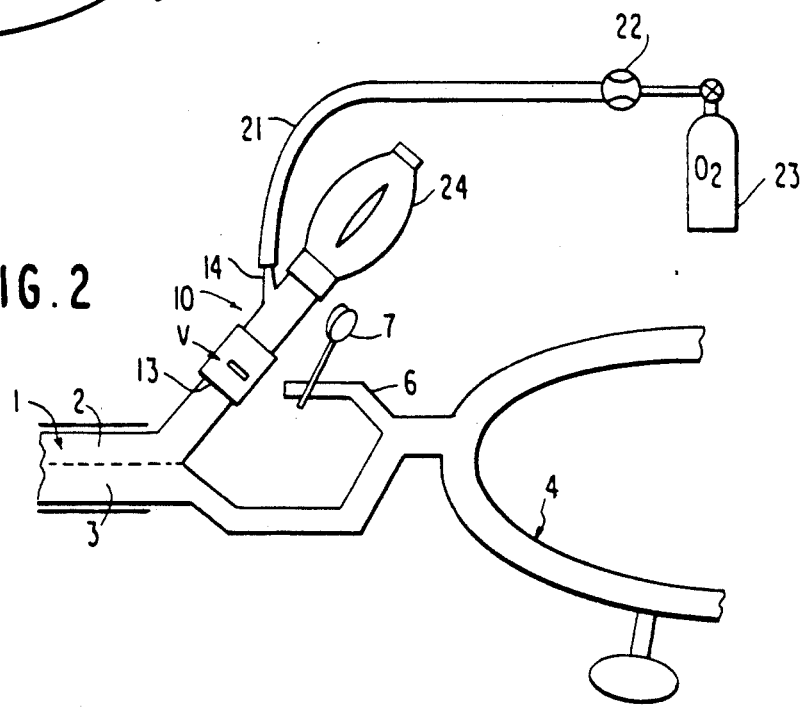
FIG. 2 is an enlarged fragmentary view showing the CPAP device of the invention connected to one-lumen of a double-lumen endotracheal tube.

The invention will now be described with reference to the drawings. As shown in FIG. 2, the continuous positive airway pressure (CPAP) device 10 is connected to the proximal end of one lumen 2 of a double-lumen endotracheal tube 1. Normally, there is inserted in the end of the lumen a 15 millimeter connector over which a 22 millimeter connector fits. Thus, a 22 millimeter diameter opening in the end of the CPAP device to be connected to the single lumen of the double-lumen endotracheal tube would be appropriate. However, it is noted that the CPAP device need not fit specifically over the 15 millimeter connector and could fit into a suction port of a double-lumen tube or into the bronchial port of the tube (neither of which is shown).

A tapered cylindrical fitting 14 extends from the side of the CPAP device and is attached to an oxygen tube 21 which, in turn, is connected to a source of oxygen 23 for delivering oxygen under pressure to the CPAP device at a constant flow rate. A flow meter 22 for indicating the rate of oxygen flow is included in the oxygen tube 21.

Figure 1:
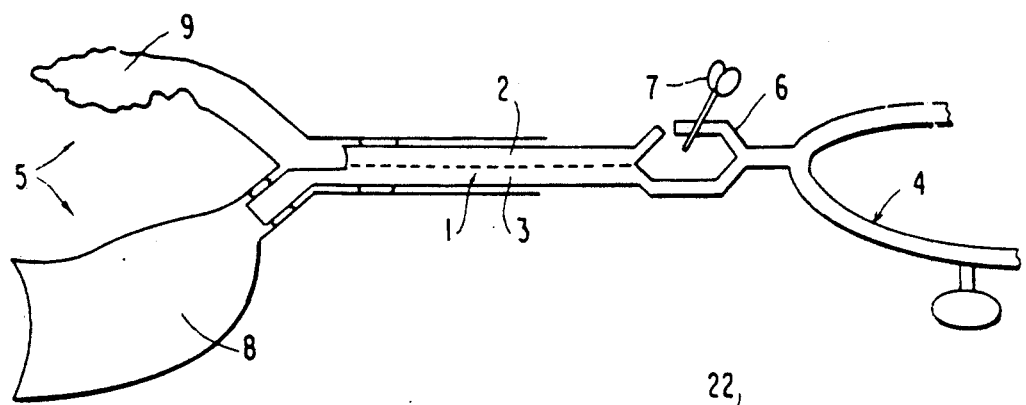
FIG. 1 is a schematic elevational view showing a double-lumen endotracheal tube inserted in a patient lying on his side.

As described with respect to FIG. 1, one leg of the Y-connector 6 is clamped by a clamp 7 for disconnecting the anesthesia circuit 4 from the lumen 2 which communicates with the non-ventilated upper lung 9.

The CPAP device of my invention also includes a ventilating means V for continuously venting at least a portion of the oxygen supplied by the source 23 to the device 10. According to the invention, the ventilating means can take different forms, as will be discussed in more detail below. An important feature of all the venting means of my invention is that there always exists an opening through which oxygen can escape, thereby avoiding a dangerous buildup of oxygen to a pressure which could cause overdistention of the non-ventilated lung 9.

Figure 3:
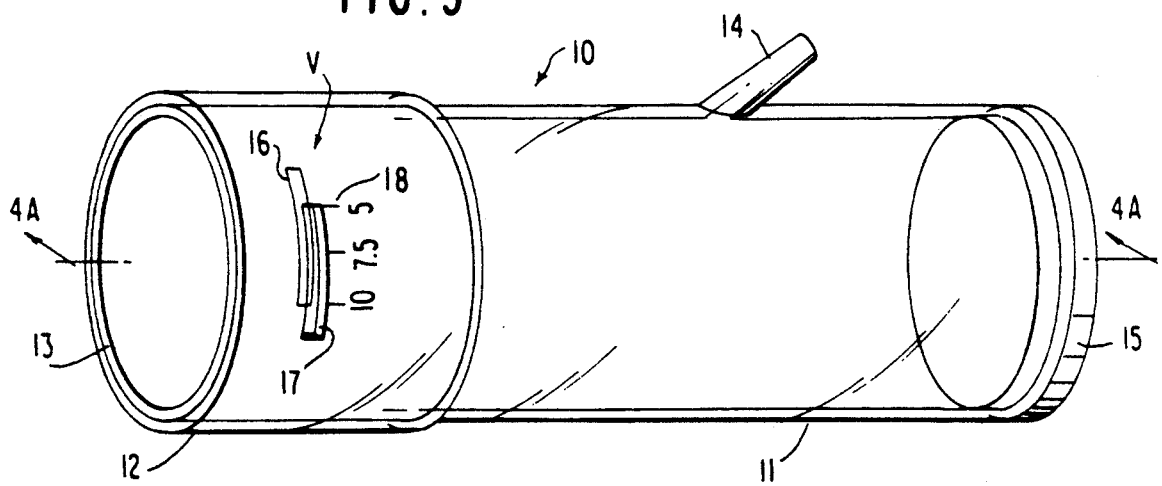
FIG. 3 is a perspective view of one embodiment of the CPAP device of the invention.

In the preferred embodiment of the invention, as shown in FIG. 3, the CPAP device includes a long hollow inner cylinder 11 which may be formed of a clear plastic, such as polyvinylchloride. Further, a shorter outer cylinder 12 is rotatably disposed snugly over the proximate end 13 of the long inner cylinder 11. Likewise, the shorter outer cylinder 12 may also be formed of a clear plastic. The end 13 of the CPAP device 10 is designed to fit onto the proximal end of one lumen of a double-lumen endotracheal tube as discussed above. The distal end of the long inner cylinder 11 is closed by a removable cap 15. Normally, the cap 15 seals the distal end of the CPAP device 10. The cap 15 may be removed in order to slide the end of an anesthesia bag 24 (FIG. 2) over the end of the device. The bag would then fill with oxygen under pressure and, if squeezed, would be used to inflate the lung to which the CPAP device is attached.

As noted above, the CPAP device includes a tapered cylindrical fitting 14 which extends from the side of the long inner cylinder 11. The oxygen tube 21 is then attached to the fitting 14 to couple the device to the source 23 of oxygen.

Both the inner and outer cylinders of the CPAP device have elongated slots 16 and 17, respectively, which are aligned longitudinally such that, when the inner and outer cylinders are rotated with respect to one another, the slots line up to allow the venting of varying degrees of oxygen under pressure. Hence, by rotating the inner and outer cylinders with respect to each other, the vent opening becomes larger or smaller, depending upon the overlap of the slots 16 and 17. With the vent opening V maximally closed off, the greatest amount of pressure is generated within the system. On the other hand, with the slots 16 and 17 lined up so as to form the largest opening, the least amount of pressure is generated within the system.

As shown in FIG. 4A, the shorter outer cylinder 12 is rotatably disposed on the long inner cylinder 11 so as to be retained by friction in a position to which it is manually rotated. However, as shown in FIGS. 4B and 4C, the long inner cylinder may be formed with a projection 19 formed on its outer circumference. The projection 19 is engageable with one of a plurality of corresponding notches 20 formed on the inner circumference of the short outer cylinder. In this manner, as the shorter outer cylinder 12 is rotated with respect to the long inner cylinder, and the vent opening becomes larger, one of the notches 20 will catch on the projection 19 at a predetermined CPAP level (e.g., 5, 7.5, 10 cm $H_2O$ CPAP) as denoted by the element numeral 18. The projection is not required since the short outer cylinder is rotatably disposed in a snug manner on the long inner cylinder. Also, an annular rib 25 may be included to engage with a corresponding groove 26 to aid in retaining the short outer cylinder in place.

FIGS. 5–7 illustrate additional embodiments in which alternative forms of the venting means V are employed.

In a second embodiment, as shown in FIG. 5, the CPAP device 110 comprises a single hollow cylindrical member 111. Again, the cylinder is preferably formed of a plastic, such as polyvinylchloride. As with the previous embodiment, the proximal end 113 of the cylindrical member 111 is connected to a single lumen of a double-lumen endotracheal tube. A tapered cylindrical fitting 114, for connection with an oxygen tube, and a removable cap 115 are likewise included.

In this embodiment, the venting means V takes the form of an elongated slot 116 passing through the wall of the cylindrical member 111 and extending in the longitudinal direction thereof. A slidable plastic tab 112 is disposed in the slot 116. The tab 112 has a gripping means 117 which may be grasped by the user of the device and pushed or pulled in the longitudinal direction so as to form a smaller or larger vent opening 116. Thus, oxygen under constant, non-varying low levels of positive airway pressure may be transmitted to the non-ventilated lung of a patient during thoracic surgery. Predetermined CPAP levels are indicated by index marks 118 formed on the outer surface of the cylindrical member 111 adjacent to the slot 116.

FIG. 6 illustrates another embodiment of the CPAP device. Structural elements similar to those illustrated for the previous embodiments are designated by the same reference numerals but preceded by the numeral 2. The CPAP device 210 is identical to the embodiment shown in FIG. 5 with the exception of the venting means V. In this instance, the venting means takes the form of a plurality of holes 216 of specific calibers (e.g., 5, 7.5, 10 cm $H_2O$ CPAP) and passing through a hollow cylindrical member 211. The holes 216 are spaced apart and arranged in a straight line so as to extend longitudinally of the hollow cylindrical member 211. Further, a tab or strip of plastic 212 has a plurality of plastic buttons or pins 217 formed thereon to serve as closure means for the corresponding holes 216. Again, there is always at least one hole open to allow continuous venting of oxygen. In operation, as the tab 212 is pulled and additional holes 216 are opened up, less CPAP is produced.

In a still further embodiment, as shown in FIG. 7, again the CPAP device is identical to the embodiments of FIGS. 5 and 6 with the exception of the venting means V. Again, identical structural elements as described in previous embodiments are designated with the same reference numerals but preceded by the numeral 3. In this embodiment, the hollow cylindrical member 311 is again formed with a series of holes 316 of specific calibers. The holes 316 are spaced apart and extend in a straight line longitudinally of the hollow cylindrical member 311. Further, several pins or buttons 312 serve as closure members to individually close the holes 316. Again, there is always at least one hole 316 open to provide venting of oxygen. Therefore, with the closing of each additional hole 316 with an individual button 312, the CPAP level in turn increases and vice versa.

From the above, it is clear that the embodiments disclosed in FIGS. 3 and 5 produce infinitely varying levels of CPAP, going from the highest to the lowest level, while the embodiments of FIGS. 6 and 7 produce a limited number of discrete levels of CPAP.

The CPAP device according to my invention includes the following advantages:

(1) It is a self-contained device which consists of a single piece of equipment.
(2) It is small, lightweight, and easier to use than alternative, bulky, cumbersome systems.
(3) It is sterile and hygenic.
(4) It eliminates the need for a pressure gauge which is common in the previous "homemade" systems.
(5) It will be easily available to practitioners since it will come packaged with each double-lumen endotracheal tube.
(6) It is inexpensive.
(7) It is safer to use than the "homemade" systems. The alternative prior art systems employ a "pop-off" valve which can be fully closed, allowing a dangerous buildup of pressure within the CPAP system and the lung to which it is attached. In my invention, there is always some degree of venting present and thus dangerous pressure levels cannot occur.
(8) It is easier to use than the previously described systems since it has graduated settings to give a precise amount of CPAP without the need to precisely adjust a pop-off valve knob while inspecting a pressure gauge.
(9) An attachment for an anesethesia bag allows the option of transiently delivering a higher pressure than the system would ordinarily deliver. This results in opening up previously collapsed alveoli. The CPAP then keeps the alveoli from collapsing.
(10) It is disposable.
(11) Its size and shape make it uniquely compatible for attachment to a single lumen of a double-lumen endotracheal tube.

It is contemplated that numerous modifications may be made to the CPAP device of my invention without departing from the spirit and scope of the invention as defined in the following claims.

What is claimed is:

1. A device for use with a single lumen of a double-lumen endotracheal tube to transmit oxygen under continuous positive airway pressure to a single non-ventilated lung of a patient during thoracic surgery, said device comprising:
    (a) a long hollow cylindrical member having one end connected to said single lumen of said double-lumen endotracheal tube, and having a closed opposite end;
    (b) means extending from said hollow cylindrical member for coupling said device to a source of oxygen delivered at a constant flow rate; and
    (c) venting means for continuously venting at least a portion of the oxygen delivered by said source to said device, said venting means being adjustable to provide for varying degrees of pressure of the oxygen delivered to said single lumen and being incapable of being completely closed off, said venting means having calibration means indicating pressure levels of the delivered oxygen without a pressure gauge;

wherein said device is a self-contained disposable unit.

2. The device according to claim 1, wherein said venting means comprises: a shorter outer cylindrical member rotatably disposed on said one end of said hollow cylindrical member; and first and second elongated slots formed in both said shorter outer cylindrical member and said hollow cylindrical member, respectively, and aligned with one another such that, when said cylindrical members are rotated relative to each other, said first and second slots cooperate to form a larger or smaller opening but always with some degree of opening of said venting means.

3. The device according to claim 1, wherein said venting means comprises: an elongated slot in said hollow cylindrical member; and a tab slidably mounted in said slot to form a larger or smaller opening but always with some degree of opening of said elongated slot.

4. The device according to claim 1, wherein said venting means comprises: a plurality of aligned holes in said hollow cylindrical member; and a plastic strip having a plurality of projections thereon for sealingly engaging and blocking a variable number of said holes but always with at least one hole being open.

5. The device according to claim 1, wherein said venting means comprises: a plurality of holes in said hollow cylindrical member; and a plurality of corresponding individual closure members for closing a variable number of said holes but always with at least one hole being open.

6. The device according to claim 1, wherein said device is formed of plastic.

7. The device according to claim 6, wherein said plastic is polyvinylchloride.

8. The device according to claim 1, wherein said opposite end of said hollow cylindrical member is closed with a removable cap.

9. The device according to claim 8, wherein when said cap is removed, said opposite end is closed by an anesthesia bag.

10. The device according to claim 1, wherein said means for coupling said device to said source of oxygen is a tapered cylindrical fitting extending from a side portion of said hollow cylindrical member and attachable to an oxygen tube.

11. The device according to claim 2, wherein said shorter outer cylinder is rotatably disposed snugly on said hollow cylindrical member so as to be retained by friction in a position to which it is manually rotated.

12. The device according to claim 2, wherein said hollow cylindrical member has a projection and said shorter outer cylindrical member has a plurality of corresponding notches which catch said projection at predetermined CPAP levels.

13. A device for use with a single lumen of a double-lumen endotracheal tube to transmit oxygen under continuous positive airway pressure to a single non-ventilated lung of a patient during thoracic surgery, said device comprising:

(a) a long hollow inner cylinder having one end connected to said single lumen of said double-lumen endotracheal tube, and having an opposite end openably closed by a removable cap;

(b) a shorter outer cylinder rotatably disposed snugly over said one end of said long inner cylinder;

(c) a cylindrical fitting extending from a side portion of said long inner cylinder for attachment to an oxygen tube for coupling said device with a source of oxygen delivered at a constant flow rate; and (d) an adjustable opening for continuously venting at least a portion of the oxygen delivered by said source to said device, wherein said adjustable opening is formed by first and second elongated slots which are provided in said inner and outer cylinders, respectively, and which are aligned with one another such that, when the inner and outer cylinders are rotated relative to each other, said slots cooperate to form a larger or smaller opening to provide varying degrees of pressure of the oxygen delivered to said single lumen, and further wherein said adjustable opening is incapable of being completely closed off and has calibration means indicating pressure levels of the delivered oxygen without a pressure gauge.

14. The device according to claim 13, wherein said device is a self-contained disposable unit formed of plastic.

15. The device according to claim 1, wherein said calibration means indicates discrete, predetermined levels of pressure of the delivered oxygen.

* * * * *